(12) United States Patent
De Man et al.

(10) Patent No.: US 7,639,774 B2
(45) Date of Patent: Dec. 29, 2009

(54) METHOD AND APPARATUS FOR EMPLOYING MULTIPLE AXIAL-SOURCES

(75) Inventors: Bruno De Man, Clifton Park, NY (US); Samit Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 216 days.

(21) Appl. No.: 10/744,027

(22) Filed: Dec. 23, 2003

(65) Prior Publication Data

US 2005/0135550 A1 Jun. 23, 2005

(51) Int. Cl.
*A61B 6/03* (2006.01)
*H05G 1/60* (2006.01)
(52) U.S. Cl. .............................. 378/9; 378/124; 378/134
(58) Field of Classification Search ............... 378/5, 378/9, 10, 11, 16, 92, 124, 134, 15, 137
See application file for complete search history.

(56) References Cited

U.S. PATENT DOCUMENTS

| | | | |
|---|---|---|---|
| 2,340,500 A | | 2/1944 | Zunick et al. |
| 3,752,989 A | * | 8/1973 | Motz et al. ............... 378/137 |
| 4,057,725 A | | 11/1977 | Wagner |
| 4,196,352 A | | 4/1980 | Berninger et al. |
| 4,274,005 A | | 6/1981 | Yamamura et al. |
| 4,284,896 A | | 8/1981 | Stonestrom |
| 4,384,359 A | | 5/1983 | Franke |
| 4,547,892 A | | 10/1985 | Richey et al. |
| 4,947,412 A | | 8/1990 | Mattson |
| 4,965,726 A | | 10/1990 | Heuscher et al. |
| 4,991,190 A | | 2/1991 | Mori |
| 5,166,961 A | | 11/1992 | Brunnett |
| 5,175,754 A | | 12/1992 | Casey et al. |
| 5,228,070 A | | 7/1993 | Mattson |
| 5,259,012 A | | 11/1993 | Baker et al. |
| 5,262,946 A | | 11/1993 | Heuscher |
| 5,276,614 A | | 1/1994 | Heuscher |
| 5,305,363 A | | 4/1994 | Burke et al. |
| 5,377,249 A | | 12/1994 | Wiesent et al. |
| 5,383,231 A | | 1/1995 | Yamagishi |
| 5,396,418 A | | 3/1995 | Heuscher |

(Continued)

OTHER PUBLICATIONS

B. D. Cullity and S. R. Stock. Elements of X-Ray Diffraction, third edition (NJ: Prentice Hall, 2001), p. 4-11.*

(Continued)

*Primary Examiner*—Allen C. Ho
(74) *Attorney, Agent, or Firm*—Fletcher Yoder

(57) ABSTRACT

A technique is provided for improving z-axis coverage and/or reducing cone beam artifacts during CT imaging. Multiple X-ray emission points are provided along the z-axis. Some or all of the emission points may be concurrently active. X-rays from concurrently active emission points are collimated so that X-rays from two or more emission points do not overlap on the detector. In addition, different groups of concurrently activated emission points may be sequentially or alternately activated, in conjunction with collimation, to prevent the overlap of X-rays from different emission points on the detector. In this manner, The X-rays may be timed and collimated such that the respective streams of radiation become adjacent at different locations, such as at the detector, the isocenter, or edge of the field of view.

31 Claims, 2 Drawing Sheets

U.S. PATENT DOCUMENTS

| | | | |
|---|---|---|---|
| 5,412,562 A | 5/1995 | Nambu et al. | |
| 5,438,605 A | 8/1995 | Burke et al. | |
| 5,485,493 A | 1/1996 | Heuscher et al. | |
| 5,491,734 A | 2/1996 | Boyd et al. | |
| 5,544,212 A | 8/1996 | Heuscher | |
| 5,570,403 A | 10/1996 | Yamazaki et al. | |
| 5,633,906 A | 5/1997 | Hell et al. | |
| 5,654,995 A | 8/1997 | Flohr | |
| 5,719,914 A | 2/1998 | Rand et al. | |
| 5,764,721 A | 6/1998 | Light et al. | |
| 5,848,117 A | 12/1998 | Urchuk et al. | |
| 5,966,422 A | 10/1999 | Dafni et al. | |
| 6,002,738 A | 12/1999 | Cabral et al. | |
| 6,047,040 A | 4/2000 | Hu et al. | |
| 6,125,167 A * | 9/2000 | Morgan | 378/124 |
| 6,130,929 A | 10/2000 | Saha | |
| 6,183,139 B1 | 2/2001 | Solomon et al. | |
| 6,208,711 B1 | 3/2001 | Rand et al. | |
| 6,229,870 B1 * | 5/2001 | Morgan | 378/9 |
| 6,233,308 B1 | 5/2001 | Hsieh | |
| 6,236,705 B1 | 5/2001 | Stergiopoulos et al. | |
| 6,236,709 B1 * | 5/2001 | Perry et al. | 378/57 |
| 6,252,924 B1 | 6/2001 | Davantes et al. | |
| 6,259,765 B1 * | 7/2001 | Baptist | 378/136 |
| 6,272,200 B1 | 8/2001 | Pan et al. | |
| 6,333,968 B1 * | 12/2001 | Whitlock et al. | 378/136 |
| 6,353,653 B1 | 3/2002 | Edic | |
| 6,363,134 B1 * | 3/2002 | Suzuki | 378/15 |
| 6,385,282 B1 | 5/2002 | Francke et al. | |
| 6,421,412 B1 * | 7/2002 | Hsieh et al. | 378/9 |
| 6,453,003 B1 * | 9/2002 | Springer et al. | 378/57 |
| 6,459,755 B1 | 10/2002 | Li | |
| 6,466,640 B1 | 10/2002 | Taguchi | |
| 6,522,712 B1 | 2/2003 | Yavuz et al. | |
| 6,529,574 B1 | 3/2003 | Hsiech | |
| 6,535,570 B2 | 3/2003 | Stergiopoulos et al. | |
| 6,674,837 B1 | 1/2004 | Taskar et al. | |
| 6,731,716 B2 | 5/2004 | Mihara et al. | |
| 6,754,300 B2 * | 6/2004 | Hsieh et al. | 378/16 |
| 6,760,399 B2 * | 7/2004 | Malamud | 378/9 |
| 6,795,521 B2 | 9/2004 | Hsu et al. | |
| 6,807,248 B2 | 10/2004 | Mihara et al. | |
| 6,914,959 B2 * | 7/2005 | Bailey et al. | 378/65 |
| 6,922,457 B2 * | 7/2005 | Nagata et al. | 378/19 |
| 6,934,357 B2 | 8/2005 | Boyd et al. | |
| 6,947,522 B2 * | 9/2005 | Wilson et al. | 378/125 |
| 6,975,703 B2 * | 12/2005 | Wilson et al. | 378/124 |
| 7,042,975 B2 * | 5/2006 | Heuscher | 378/8 |
| 2002/0025017 A1 | 2/2002 | Stergiopoulos et al. | |
| 2002/0074929 A1 | 6/2002 | Taskar et al. | |
| 2002/0085674 A1 | 7/2002 | Price et al. | |
| 2002/0094064 A1 | 7/2002 | Zhou et al. | |
| 2003/0043957 A1 | 3/2003 | Pelc | |
| 2003/0118155 A1 | 6/2003 | Ueno et al. | |
| 2004/0114710 A1 | 6/2004 | Ozaki | |
| 2004/0136490 A1 | 7/2004 | Edic et al. | |
| 2004/0213378 A1 | 10/2004 | Zhou et al. | |
| 2005/0089134 A1 * | 4/2005 | Bruder et al. | 378/9 |
| 2005/0100126 A1 * | 5/2005 | Mistretta et al. | 378/15 |
| 2005/0135550 A1 | 6/2005 | De Man et al. | |
| 2005/0175143 A1 * | 8/2005 | Miyazaki et al. | 378/19 |
| 2006/0002506 A1 | 1/2006 | Pelc | |

OTHER PUBLICATIONS

Lalush, David C., Feasibility of Transmission Micro-CT with Two Fan-Beam Sources, IEEE, pp. 1283-1286, Sep. 1-5, 2004, vol. 4, San Francisco, California.

* cited by examiner

METHOD AND APPARATUS FOR EMPLOYING MULTIPLE AXIAL-SOURCES

BACKGROUND OF THE INVENTION

The present invention relates generally to the field of non-invasive imaging and more specifically to the field of computed tomography. In particular, the present invention relates to improving z-axis coverage using collimation and timing techniques.

CT scanners operate by projecting fan shaped or cone shaped X-ray beams from an X-ray source. The X-ray source emits X-rays at numerous angles relative to an object being imaged, such as a patient, which attenuates the X-ray beams as they pass through. The attenuated beams are detected by a set of detector elements, which produce signals representing the attenuation of the incident X-ray beams. The signals are processed to produce data representing the line integrals of the attenuation coefficients of the object along the X-ray paths. These signals are typically called "projection data" or just "projections". By using reconstruction techniques, such as filtered backprojection, useful images may be formulated from the projections. The images may in turn be associated to form a volume rendering of a region of interest. In a medical context, pathologies or other structures of interest may then be located or identified from the reconstructed images or rendered volume.

It is generally desirable to develop CT scanners with high spatial and temporal resolution, good image quality, and good coverage along the z-axis, i.e., the long or rotational axis of the CT scanner. To meet some or all of these objectives, it may be desirable to increase the coverage provided by the detector, thereby allowing greater scan coverage in one or more dimensions. For example, z-axis coverage of the detector may be improved by increasing the number of rows of detector elements in the detector.

This approach has lead to the development of CT systems with larger detectors. Larger detectors, however, may be undesirable for a variety of reasons. For example, as one might expect, larger detectors are both more costly and more difficult to produce. In addition, the mechanical subsystem responsible for supporting and/or rotating a larger detector may also need to be larger and more complex and/or may be subject to greater mechanical stress. Furthermore, larger detectors are associated with larger cone angles, i.e., the angle between the source and the detector periphery. The increased cone angle between the source and detector periphery is associated with increased cone beam artifacts in the reconstructed images, particularly in axial scan modes. When the cone angle increases beyond a certain limit, the degradation of the image quality may become severe. For this reason, it may be difficult to increase the z-axis coverage by simply increasing the coverage of the detector in the direction of the z-axis.

One alternative has been to move the source further from the object or patient, to minimize magnification, thereby reducing cone angle. Increasing the source distance, however, may not be physically feasible. Another alternative has been to increase the detector element size along the periphery to reduce or maintain the number of detector channels, i.e., the total number of detector elements. Increasing the size of detector elements, however, may reduce the overall resolution of the CT system beyond what is desired or acceptable. A further alternative has been to employ multiple X-say sources along the z-axis that are sequentially activated. In this configuration, however, each source illuminates the full detector when active, resulting in large cone angles and the generation of cone beam artifacts in the reconstructed images. A technique for improving z-axis coverage without image degradation may therefore be desirable.

BRIEF DESCRIPTION OF THE INVENTION

The present technique provides a novel method and apparatus for increasing coverage along the z-axis. Multiple X-ray sources along the z-axis are provided by the technique. The X-ray sources may be collimated such that only a portion of the detector is illuminated by X-rays from a respective source. Because of the collimation, the X-ray sources may be concurrently active without regions of overlapping incident radiation. In this manner, z-axis coverage may be improved without a corresponding increase in cone angle. Fewer cone beam artifacts may, therefore, be present in the reconstructed images.

In accordance with one aspect of the present technique, a method is provided for imaging a volume. In accordance with this aspect, X-rays from two or more emission points which are axially-offset along a z-axis are concurrently emitted at each view angle of interest. The concurrently emitted X-rays may be collimated such that X-rays from more than one emission point do not concurrently impact a region of a detector array. Systems and computer programs that afford functionality of the type defined by these methods are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
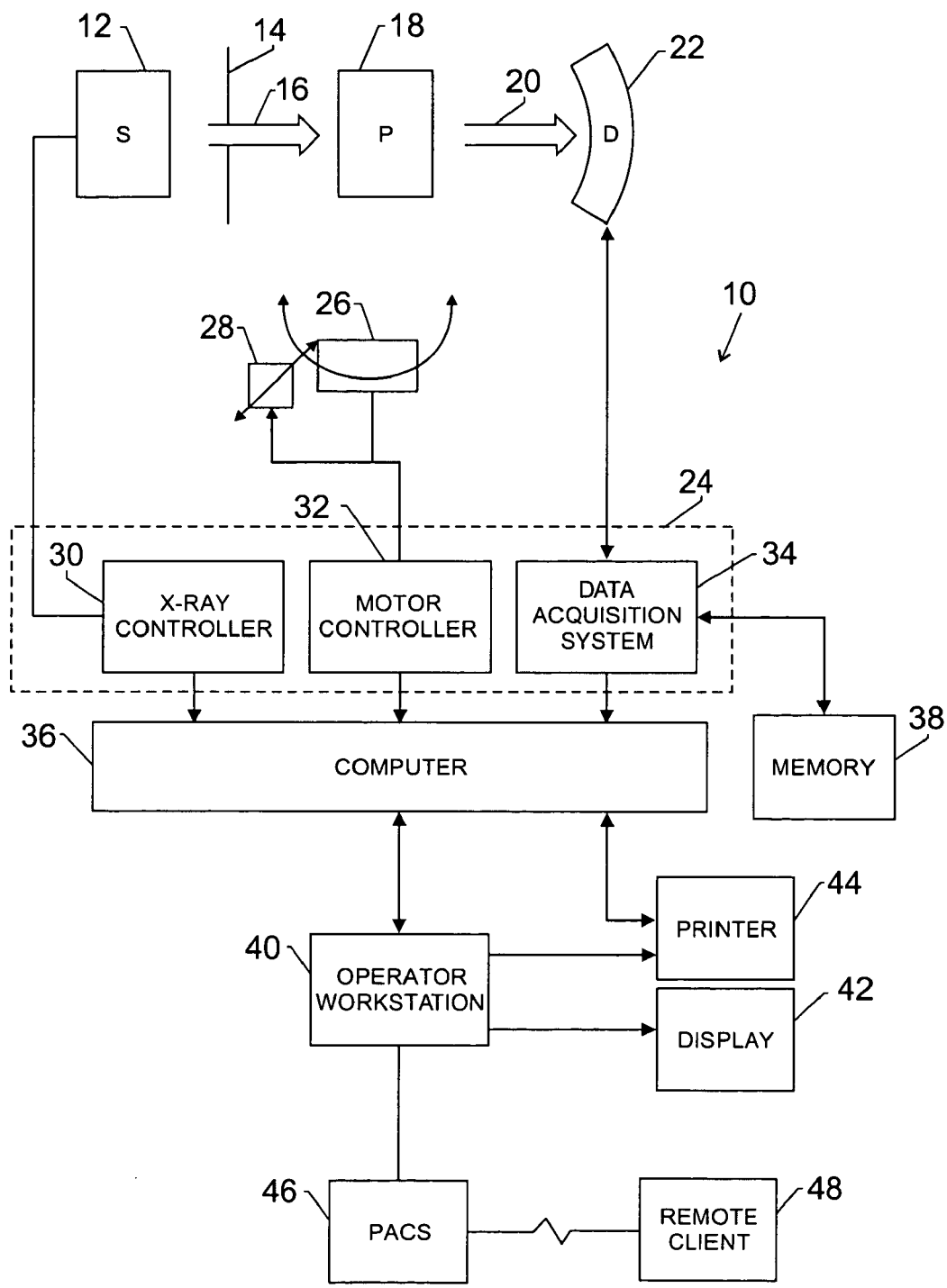
FIG. 1 is a diagrammatical view of an exemplary imaging system in the form of a CT imaging system for use in producing processed images, in accordance with one aspect of the present technique.

FIG. 1 illustrates diagrammatically an imaging system 10 for acquiring and processing image data. In the illustrated embodiment, system 10 is a computed tomography (CT) system designed to acquire X-ray projection data, to reconstruct the projection data into an image, and to process the image data for display and analysis in accordance with the present technique. Though the imaging system 10 is discussed in the context of medical imaging, the techniques and configurations discussed herein are applicable in other non-invasive CT imaging contexts, such as baggage or package screening. In the embodiment illustrated in FIG. 1, CT imaging system 10 includes a source 12 of X-ray radiation. As discussed in detail herein, the source 12 of X-ray radiation may be any distributed source configured to emit X-rays from different z-locations. For example, the X-ray source 12 may consist of multiple X-ray tubes arranged at different locations along the z-axis. Similarly, the X-ray source 12 may include one or more addressable solid-state sources. Such solid-state sources may be configured as arrays of field emitters, including one-dimensional arrays, i.e., lines, and two-dimensional arrays.

The X-ray source 12 may be positioned proximate to a collimator 14. The collimator 14 may consist of one or more collimating regions, such as lead or tungsten shutters, for each emission point of the source 12. The collimator 14 typically defines the size and shape of the one or more streams of radiation 16 that pass into a region in which a subject, such as a human patient 18 is positioned. A stream of radiation 16 may be generally cone shaped, depending on the configuration of the detector array, discussed below, as well as the desired method of data acquisition. An attenuated portion of the radiation 20 passes through the subject, which provides the attenuation, and impacts a detector array, represented generally at reference numeral 22.

The detector 22 is generally formed by a plurality of detector elements, which detect the X-rays that pass through and around a subject of interest. Each detector element produces an electrical signal that represents the intensity of the X-ray beam at the position of the element during the time the beam strikes the detector. Typically, signals are acquired at a variety of angles around the subject of interest so that a plurality of radiographic views may be collected. These signals are acquired and processed to reconstruct an image of the features within the subject, as described below.

The X-ray source 12 is controlled by a system controller 24, which furnishes power, focal spot location, control signals and so forth for CT examination sequences. Moreover, the detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, and associated memory circuitry. The associated memory circuitry may store programs and routines executed by the computer, configuration parameters, image data, and so forth.

In the embodiment illustrated in FIG. 1, system controller 24 may control the movement of a linear positioning subsystem 28 and rotational subsystem 26 via a motor controller 32. In imaging systems 10 in which the source 12 and/or the detector 22 may be rotated, the rotational subsystem 26 may rotate the X-ray source 12, the collimator 14, and/or the detector 22 through one or multiple turns around the patient 18. It should be noted that the rotational subsystem 26 might include a gantry. The linear positioning subsystem 28 enables the patient 18, or more specifically a patient table, to be displaced linearly. Thus, the patient table may be linearly moved within the gantry or within the stationary source 12 and/or detector 22 to generate images of particular areas of the patient 18. In embodiments comprising a stationary source 12 and a stationary detector 22, the rotational subsystem 26 may be absent. Similarly, in embodiments in which the source 12 and the detector 22 are configured to provide extended coverage along the z-axis, i.e, the axis associated with the main length of the patient 18, the linear positioning subsystem 28 may be absent.

As will be appreciated by those skilled in the art, the distributed source 12 of radiation may be controlled by an X-ray controller 30 disposed within the system controller 24. The X-ray controller 30 may be configured to provide power and timing signals to the X-ray source 12. In addition, the X-ray controller may be configured to selectively activate the distributed X-ray source 12 such that tubes or emitters at different locations along the z-axis may be concurrently activated.

Further, the system controller 24 may comprise a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor-based system, such as a computer 36.

The computer 36 is typically coupled to the system controller 24. The data collected by the data acquisition system 34 may be transmitted to the computer 36 for subsequent processing and reconstruction. For example, the data collected from the detector 22 may undergo pre-processing and calibration at the data acquisition system 34 and/or the computer 36 to condition the data to represent the line integrals of the attenuation coefficients of the scanned objects. The processed data, commonly called projections, may then be filtered and backprojected to formulate an image of the scanned area. Once reconstructed, the image produced by the system of FIG. 1 reveals an internal region of interest of the patient 18 which may be used for diagnosis, evaluation, and so forth.

The computer 36 may comprise or communicate with a memory 38 that can store data processed by the computer 36 or data to be processed by the computer 36. It should be understood that any type of computer accessible memory device capable of storing the desired amount of data and/or code may be utilized by such an exemplary system 10. Moreover, the memory 38 may comprise one or more memory devices, such as magnetic or optical devices, of similar or different types, which may be local and/or remote to the system 10. The memory 38 may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 which may be equipped with a keyboard and/or other input devices. An operator may thereby control the system 10 via the operator workstation 40. Thus, the operator may observe the reconstructed image and other data relevant to the system from computer 36, initiate imaging, and so forth.

A display 42 coupled to the operator workstation 40 may be utilized to observe the reconstructed image. Additionally, the scanned image may be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image data.

One or more operator workstations 40 may be linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The CT imaging system 10 described above may be modified or configured in a variety of ways to improve spatial and temporal resolution, to improve image quality, and/or to improve z-axis coverage. Indeed, various source 12 and detector 22 configurations may be implemented which improve one or more of these parameters. For example, the distributed X-ray source 12 may include more than one addressable emission point, such as an X-ray tube or field emitter, along the z-axis (typically the axis of rotation or the axis running through the bore of the scanner) to improve or increase z-axis coverage.

Figure 2:
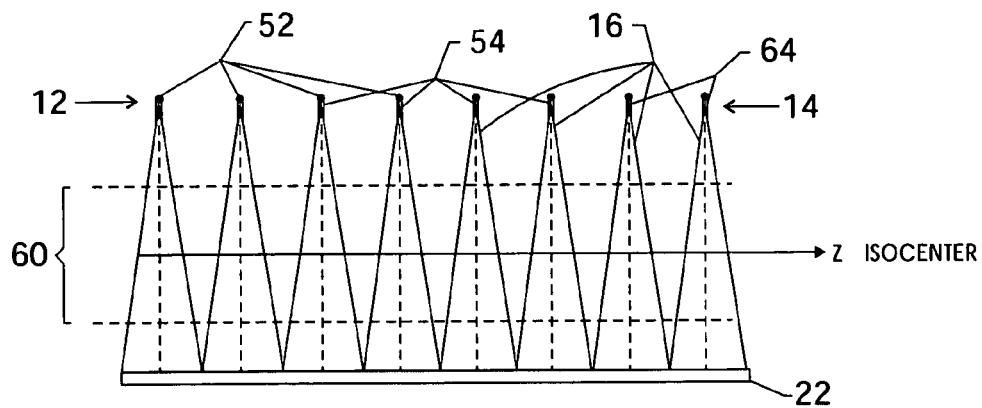
FIG. 2 depicts the collimation and activation of X-ray sources positioned along the z-axis of an exemplary CT imaging system such that the X-rays streams are adjacent at the detector array, in accordance with one aspect of the present technique.
Figure 3:
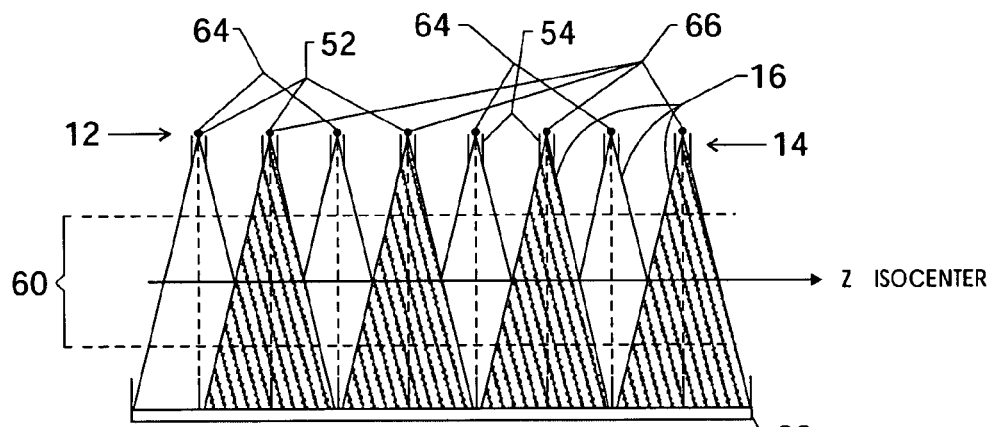
FIG. 3 depicts the collimation and alternating activation of groups X-ray sources positioned along the z-axis of an exemplary CT imaging system such that the X-rays streams are adjacent at the isocenter, in accordance with one aspect of the present technique.
Figure 4:
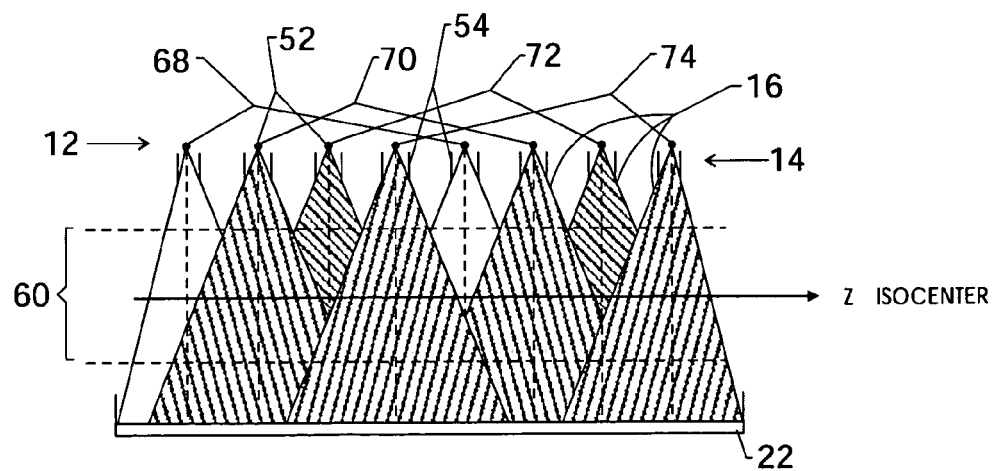
FIG. 4 depicts the collimation and alternating activation of groups X-ray sources positioned along the z-axis of an exemplary CT imaging system such that the X-rays streams are adjacent at the edge of the field of view, in accordance with one aspect of the present technique.

Such a configuration is depicted in FIGS. 2-4. The timing and collimation of the depicted emission points 52 of the X-ray source 12 may be adjusted so that, at any point in time, radiation streams 16 generated by the different emissions points 52 do not concurrently impacts the same detector elements of the detector 22. With regard to collimation, the respective collimator openings, defined by X-ray opaque shutters 54, may be adjusted so that the different radiation streams 16 become adjacent at a certain distance from the X-ray source 12, such as at the isocenter or the edge of the field of view 60. With regard to timing, the respective emission points 52 may be differentially activated such that, based upon the selected degree of collimation, the respective radiation streams 16 do not overlap when impacting the detector 22. The proposed activation pattern can be repeated for each view, although, in some cases, it may be desirable to use different activation patterns for different views.

For example, at one extreme, each radiation stream 16 may be collimated such that it illuminates the entire detector 22. In this example, the sources 12 must be activated sequentially, i.e., no sources 12 may be concurrently active. At the other extreme, as depicted in FIG. 2, each radiation stream 16 may be collimated to impact the detector 22 in adjacent or substantially adjacent regions. In this example, all of the emission points 52 of the X-ray source 12 may be activated simultaneously. Furthermore, collimation of consecutive radiation streams 16 to be adjacent at the detector 22 allows anti-scatter septa along the z-axis at the detector 22.

Alternatively, as depicted in FIG. 3, consecutive radiation streams 16 may be collimated so that they become adjacent at the isocenter. In this example, consecutive radiation streams 16 would overlap at the detector 22 if the respective sources were activated concurrently. To prevent overlap of the radiation streams 16 at the detector 22, the emission points 52 may be split into at least two groups, as depicted by the first group 64 and second group 66 of FIG. 3, and the groups of emission points 52 alternately activated for the desired views. Sufficient image data to reconstruct the field of view 60 may be obtained by one full rotation of rotatable emission points 52, such as conventional X-ray tubes or solid-state arc sources. Alternately, for stationary distributed sources 12, sufficient image data may be obtained by a full 360° activation cycle of the stationary source, such as a solid-state ring source. Furthermore, collimation of consecutive radiation streams 16 to be adjacent at the isocenter allows anti-scatter septa along the z-axis at particular locations.

Similarly, as depicted in FIG. 4, consecutive radiation streams 16 may be collimated so that they become adjacent when entering the field of view 60. To prevent overlap of the radiation streams 16 at the detector 22, the emission points 52 may be split into at least four groups, as depicted by the first group 68, second group 70, third group 72, and fourth group 74 of FIG. 4, and the groups of emission points 52 activated in an alternating manner for the desired views. Sufficient image data to reconstruct the field of view 60 may be obtained by at least a half-scan acquisition by rotatable emission points 52, i.e., 180°+α of rotation. Similarly, for a suitable stationary source, sufficient image data may be acquired by a 180°+α activation cycle of the respective emission points 52.

One advantage of utilizing multiple emission points 52 along the z-axis is that a large volume may be reconstructed, with no or limited cone beam artifacts, based on a single axial scan. Compared to the configurations where each radiation stream 16 illuminates the entire detector 22, the preceding technique allows more uniform sampling and more uniform patient dose. Furthermore, although helical scanning techniques may allow for large cone angles, it does not allow the scanner to efficiently cover the same volume repeatedly, as may be needed for imaging dynamic tissues. The use of multiple X-ray sources 12 along the z-axis, however, provides efficient sampling of the same volume. In addition, the present technique allows for the efficient use of the detector 22, as the potential z-coverage associated with a scan is substantially equal to the size of the detector 22. The present technique also allows for the possibility of reducing scatter by the use of suitable anti-scatter grids between concurrently emitted streams of radiation 16.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A CT imaging system, comprising:
an X-ray source comprising a plurality of emission points, each emission point comprising a respective X-ray tube and configured to emit respective X-ray beams for traversing an imaging volume, wherein each of the emission points is located at the same angular position but axially offset relative to a z-axis of the CT imaging system such that if each of the plurality of emission points were to be activated concurrently, the respectively emitted X-ray beams would be directly adjacent when entering an imaging field of view, exiting the imaging field of view, or at the isocenter of the CT imaging system;
a detector array comprising a plurality of detector elements, wherein each detector element is configured to generate one or more signals in response to the respective X-ray beams;
a collimator configured to collimate the respective X-ray beams; and
a controller configured to prevent overlap of the respective X-ray beams at the detector away by activating subsets of the emission points at different times.

2. The CT imaging system of claim 1, wherein if each of the plurality of emission points were to be activated concurrently, the respectively emitted X-ray beams would overlap at the detector.

3. The CT imaging system of claim 1, wherein the subsets of emission points comprises a first subset of the emission points and a second subset of the emission points.

4. The CT imaging system of claim 3, wherein the controller is configured to alternately activate the first subset of emission points and the second subset of emission points.

5. The CT imaging system of claim 3, wherein the first and second subsets of emission points are arranged in an alternating manner along the z-axis.

6. The CT imaging system of claim 3, wherein the first and second subsets of emission points each comprise one-half the plurality of emission points in the X-ray source.

7. The CT imaging system of claim 1, wherein the subsets of emission points comprises four subsets of emission points, wherein the controller is configured to activate each of the four subsets of emission points at different respective times.

8. The CT imaging system of claim 7, wherein each of the four subsets comprises a different quarter of the plurality of emission points in the X-ray source.

9. The CT imaging system of claim 1, wherein each emission point is independently addressable.

10. The CT imaging system of claim 1, comprising a computer system configured to receive the one or more signals and to process the one or more signals to generate one or more images.

11. The CT imaging system of claim 10, comprising an operator workstation configured to display the one or more images.

12. A method for imaging a volume using an imaging system having a plurality of emission points, comprising:
sequentially activating each of a plurality of subsets of the emission points, wherein each of the plurality of emission points is configured to emit respective X-ray beams for traversing an imaging volume, wherein each of the emission points is located at the same angular position but offset in an axial direction relative to a z-axis of the imaging system such that if each subset of emission points were to be activated concurrently, the respectively emitted X-ray beams would be directly adjacent when entering an imaging field of view, exiting the imaging field of view, or at the isocenter of the imaging system, but would overlap at a detector array, and wherein the plurality of emission points remains stationary in the axial direction relative to the imaging volume during acquisition of image data.

13. The method of claim 12, wherein the concurrently emitted X-ray beams from a single subset of emission points do not overlap at the detector array.

14. The method of claim 12, comprising collimating the respectively emitted X-ray beams.

15. The method of claim 12, comprising:
generating one or more signals in response to the impact of the X-ray beams on detector elements of the detector array; and
processing the one or more signals to generate one or more images.

16. The method of claim 15, comprising displaying the one or more images.

17. The method of claim 12, wherein the subsets of emission points comprise a first subset and a second subset, and wherein sequentially activating each of the plurality of subsets of emission points comprises activating the first subset of emission points at a first time and activating the second subset of emission points in alternation.

18. The method of claim 12, wherein the plurality of subsets of emission points comprises four subsets, and wherein sequentially activating each of the plurality of subsets of emission points comprises activating a different sequential starting emission point and every forth emission point along the z-axis at respective first, second, third, and fourth times.

19. The method of claim 18, wherein each subset of emission points comprises one-quarter of the plurality of emission points.

20. The method of claim 12, wherein each emission point is independently addressable.

21. An imaging system comprising:
an X-ray source comprising a plurality of emission points axially spaced relative to a z-axis of the imaging system, each emission point comprising a respective X-ray tube, wherein each emission point is configured to emit a substantially conical X-ray beam for traversing an imaging volume, and wherein the plurality of emission points are divided into a plurality of subsets, wherein each subset comprises at least one emission point;
a detector array comprising a plurality of detector elements, wherein each detector element may generate one or more signals in response to the respective conical X-ray beams;
a collimator configured to collimate the respective conical X-ray beams; and
a controller comprising a data acquisition system and configured to control the collimator, to acquire the one or more signals using the data acquisition system, and to control the X-ray source such that only one subset of emission points is activated at any time;
wherein if two or more of the plurality of subsets of emission points were to be activated concurrently, the respective conical X-ray beams concurrently emitted from the two or more subsets would be directly adjacent at some point in their respective paths, but not at the detector array.

22. The imaging system of claim 21, wherein the respective conical X-ray beams concurrently emitted from the two or more subsets of emission points would be directly adjacent when entering an imaging field of view, exiting the imaging field of view, or at the isocenter of the imaging system.

23. The imaging system of claim 21, wherein the imaging system is a CT imaging system.

24. The imaging system of claim 21, comprising a computer system configured to receive the one or more signals and to process the one or more signals to generate one or more images.

25. The imaging system of claim 24, comprising an operator workstation configured to display the one or more images.

26. The imaging system of claim 21, wherein each of the plurality of subsets comprises the same number of emission points.

27. A method for imaging a volume, comprising:
in an imaging system having a plurality of emission points divided into a plurality of subsets, selecting one of the plurality of subsets of emission points, wherein each of the subsets comprise at least one emission point;
emitting X-ray beams from the selected subset; and
collimating the emitted X-ray beams such that the X-ray beams traverse a volume to be imaged as a substantially conical beam;
wherein each of the plurality of emission points is offset in an axial direction relative to a z-axis of the imaging system, wherein if two or more of the plurality of subsets of emission points were to be activated concurrently, the respective conical X-ray beams concurrently emitted from the two or more subsets would be directly adjacent at some point in their respective paths, but not at a detector array, and wherein the plurality of emission points remains stationary in the axial direction relative to the volume to be imaged during acquisition of image data.

28. The method of claim 27, wherein the conical X-ray beams concurrently emitted from the two or more subsets of emission points would be directly adjacent when entering an imaging field of view, exiting the imaging field of view, or at the isocenter of the imaging system.

29. The method of claim 27, comprising:

generating one or more signals in response to the impact of the radiation streams on detector elements of the detector array; and processing the one or more signals to generate one or more images.

30. The method of claim 29, comprising displaying the one or more images.

31. The method of claim 27, wherein each of the plurality of subsets comprises the same number of emission points.

\* \* \* \* \*

UNITED STATES PATENT AND TRADEMARK OFFICE
CERTIFICATE OF CORRECTION

PATENT NO. : 7,639,774 B2 Page 1 of 1
APPLICATION NO. : 10/744027
DATED : December 29, 2009
INVENTOR(S) : De Man et al.

It is certified that error appears in the above-identified patent and that said Letters Patent is hereby corrected as shown below:

In Column 6, Line 66, in Claim 1, delete "away" and insert -- array --, therefor.

Signed and Sealed this

Eighteenth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,639,774 B2 Page 1 of 1
APPLICATION NO. : 10/744027
DATED : December 29, 2009
INVENTOR(S) : Bruno De Man et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 216 days.

should read (*) Notice: Subject to any disclaimer, the term of this patent is extended or adjusted under 35 U.S.C. 154(b) by 70 days.

Signed and Sealed this

Third Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,639,774 B2
APPLICATION NO. : 10/744027
DATED : December 29, 2009
INVENTOR(S) : De Man et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 70 days.

Signed and Sealed this

Ninth Day of November, 2010

David J. Kappos
*Director of the United States Patent and Trademark Office*